United States Patent
Kim et al.

(10) Patent No.: US 11,241,170 B2
(45) Date of Patent: Feb. 8, 2022

(54) MONITOR FOR BLOOD PRESSURE AND OTHER ARTERIAL PROPERTIES

(71) Applicants: UNIVERSITY OF MARYLAND, COLLEGE PARK, College Park, MD (US); BOARD OF TRUSTEES OF MICHIGAN STATE UNIVERSITY, East Lansing, MI (US); Georgia Tech Research Corporation, Atlanta, GA (US)

(72) Inventors: Chang-Sei Kim, North Potomac, MD (US); Stephanie Lind-Ober Martin, College Park, MD (US); Jin-Oh Hahn, Rockville, MD (US); Ramakrishna Mukkamala, Okemos, MI (US); Omer T. Inan, Marietta, GA (US)

(73) Assignees: University of Maryland, College Park, College Park, MD (US); Board of Trustees of Michigan State University, East Lansing, MI (US); Georgia Tech Research Corporation, Atlanta, GA (US)

( * ) Notice: Subject to any disclaimer, the term of this patent is extended or adjusted under 35 U.S.C. 154(b) by 309 days.

(21) Appl. No.: 15/946,889

(22) Filed: Apr. 6, 2018

(65) Prior Publication Data
US 2018/0289288 A1    Oct. 11, 2018

Related U.S. Application Data

(60) Provisional application No. 62/483,113, filed on Apr. 7, 2017.

(51) Int. Cl.
*A61B 5/11*    (2006.01)
*A61B 5/00*    (2006.01)
(Continued)

(52) U.S. Cl.
CPC ........ *A61B 5/1102* (2013.01); *A61B 5/02108* (2013.01); *A61B 5/7253* (2013.01); *A61B 5/02438* (2013.01)

(58) Field of Classification Search
None
See application file for complete search history.

(56) References Cited

U.S. PATENT DOCUMENTS

| 2008/0194975 A1* | 8/2008 | MacQuarrie | A61B 5/1102 600/483 |
| 2015/0018637 A1* | 1/2015 | Chen | A61B 5/0295 600/301 |

(Continued)

OTHER PUBLICATIONS

J. Gomez-Clapers, R. Casanella and R. Pallas-Areny, "Direct Pulse Transit Time measurement from an electronic weighing scale," 2016 Computing in Cardiology Conference (CinC), Vancouver, BC, 2016, pp. 773-776. doi: 10.23919/CIC.2016.7868857.

(Continued)

*Primary Examiner* — Michael R Bloch
(74) *Attorney, Agent, or Firm* — Leveque Intellectual Property Law, P.C.

(57) ABSTRACT

A method and apparatus for monitoring arterial properties, including systolic and diastolic pressure levels, of a subject is provided, in which a hardware processor receives and analyzes ballistocardiogram (BCG) data of the subject. A non-transient computer readable medium, accessible by the hardware processor, contains instructions that, when executed by the hardware processor, identify features of the BCG waveform and determine the arterial properties therefrom. For example, a diastolic pressure level may be determined from a time interval between the 'I' and 'J' peaks of the waveform and a systolic pressure level determined from the amplitude difference between the 'J' and 'K' peaks of the waveform in combination with the 'I-J' time interval or (Continued)

amplitude difference. A physical mechanism for the BCG data is disclosed that enables other arterial properties of the subject to be determined from the BCG data alone or from the BCG data in combination with other measurements.

10 Claims, 7 Drawing Sheets

(51) Int. Cl.
*A61B 5/021* (2006.01)
*A61B 5/024* (2006.01)

(56) References Cited

U.S. PATENT DOCUMENTS

| | | | | |
|---|---|---|---|---|
| 2016/0051156 A1* | 2/2016 | Kim | ............... | A61B 5/0205 600/391 |
| 2016/0174852 A1* | 6/2016 | He | ............... | A61B 5/0285 600/301 |
| 2016/0354027 A1* | 12/2016 | Benson | ............... | B60N 2/002 |
| 2017/0281024 A1* | 10/2017 | Narasimhan | ............... | A61B 5/6824 |

OTHER PUBLICATIONS

Chang-Sei Kim, Stephanie L. Ober, M. Sean McMurtry, Barry A. Finegan, Omer T. Inan, Ramakrishna Mukkamala & Jin-Oh Hahn, "Ballistocardiogram: Mechanism and Potential for Unobtrusive Cardiovascular Health Monitoring," Scientific Reports, 6:31297, Aug. 9, 2016.

Martin et al., "Weighing Scale-Based Pulse Transit Time is a Superior Marker of Blood Pressure than Conventional Pulse Arrival Time," Scientific Reports, 6:39273, Dec. 15, 2016.

Ashouri, H., Orlandic, L. & Inan, O. T. Unobtrusive estimation of cardiac contractility and stroke volume changes using ballistocardiogram measurements on a high bandwidth force plate. Sensors 16, 787 (2016).

Inan, O. T., Etemadi, M., Paloma, A., Giovangrandi, L. & Kovacs, G. T. A. Non-invasive cardiac output trending during exercise recovery on a bathroom-scale-based ballistocardiograph. Physiol. Meas. 30, 261-274 (2009).

C.S. Kim, A.M. Carek, O.T. Inan, R. Mukkamala, J.O. Hahn, "Ballistocardiogram-Based Approach to Cuff-Less Blood Pressure Monitoring: Proof-of-Concept and Potential Challenges," IEEE Transactions on Biomedical Engineering, vol. 65, No. 11, pp. 2384-2391, Nov. 2018 [Featured Article Nov. 2018].

* cited by examiner

MONITOR FOR BLOOD PRESSURE AND OTHER ARTERIAL PROPERTIES

PRIORITY CLAIM

This application claims the benefit of Provisional Patent Application No. 62/483,113, filed Apr. 7, 2017, the contents of which are hereby incorporated by reference in their entirety.

STATEMENT REGARDING FEDERALLY SPONSORED RESEARCH OR DEVELOPMENT

This invention was made with government support under 1U01EB018818-01 awarded by the NIH. The government has certain rights in the invention.

BACKGROUND

Hypertension is one of the most prevalent chronic diseases in the Unites States and around the world. Hypertension can be treated with lifestyle changes and medication therapy, but the primary issue associated with hypertension management is that its presence is frequently missed. Unobtrusive and ubiquitous blood pressure (BP) monitoring technology could improve hypertension management and control, but such a technology has not been mature enough to be deployed at present. In fact, most existing non-invasive BP monitoring techniques used in healthcare and research (e.g., auscultation, oscillometry, volume clamping, and applanation tonometry) suffer from limited convenience, e.g., due to the requirement for an inflatable cuff.

To realize more convenient and deployable BP monitoring technologies, cuff-less BP monitoring is being widely investigated. Many of the reported techniques are built upon the principle of pulse wave velocity and pulse transit time (PTT). PTT is the time required for a BP wave to travel from one arterial site to another. An increase in BP results in a decrease in PTT, as artery stiffens with an increase in BP, increasing the velocity of travel of the BP wave. Hence, PTT is often inversely correlated with BP. Further, PTT may be simply measured as the time interval between proximal and distal arterial waveforms. Thus, PTT carries the advantage of possibly offering passive BP monitoring without using any inflatable cuff.

Despite its convenience relative to cuff-based techniques, PTT-based cuff-less BP monitoring technology may further be improved both in terms of accuracy and convenience. First, many PTT techniques frequently employ a single BP surrogate (that is, a PTT or pulse arrival time (PAT)) to monitor both diastolic (DP) and systolic (SP) pressures in the blood. Here, a 'surrogate' refers to a measurement of a phenomenon, other than blood pressure, from which blood pressure can be inferred. However, given that these BP levels are not perfectly correlated with each other, the accuracy of PTT-based techniques may be improved by employing independent BP surrogates indicative of multiple BP levels. Second, although advances have been made in the PTT/PAT instrumentation technologies, many existing techniques require the placement of two sensors on the body (e.g., electrocardiogram (ECG) as the proximal arterial waveform and a distal arterial waveform, e.g., photoplethysmogram (PPG) for PAT). Thus, the convenience of PTT-based BP monitoring techniques may be improved by reducing, or even eliminating, sensors placed on the body.

A ballistocardiogram (BCG) is a graphical representation of motions of the human body arising from the ejection of blood into the aorta with each heartbeat. While it has been recognized that a PTT is correlated with time intervals on the BCG, the BCG has not been used for blood pressure measurements because the genesis of the waves shown in BCG data has remained elusive, and thus a prediction of the BCG waves as well as physiologic timings and amplitudes of the waves has been generally unavailable. Rather, the BCG has been interpreted as a measure of ballistic forces on the heart and the mechanical movement of the heart. While the BCG has been used as a vital sign in that some heart malfunctions can be identified by observing and analyzing the BCG signal, it would be advantageous to develop and utilize models of the BCG waveform that can be used for monitoring and diagnostic tools and techniques, such as the unobtrusive monitoring and diagnosis of cardiovascular health and disease.

BRIEF DESCRIPTION OF THE DRAWINGS

The accompanying drawings provide visual representations which will be used to more fully describe various representative embodiments and can be used by those skilled in the art to better understand the representative embodiments disclosed and their inherent advantages. The drawings are not necessarily to scale, emphasis instead being placed upon illustrating the principles of the devices, systems, and methods described herein. In these drawings, like reference numerals identify corresponding elements.

DETAILED DESCRIPTION

Figure 1:
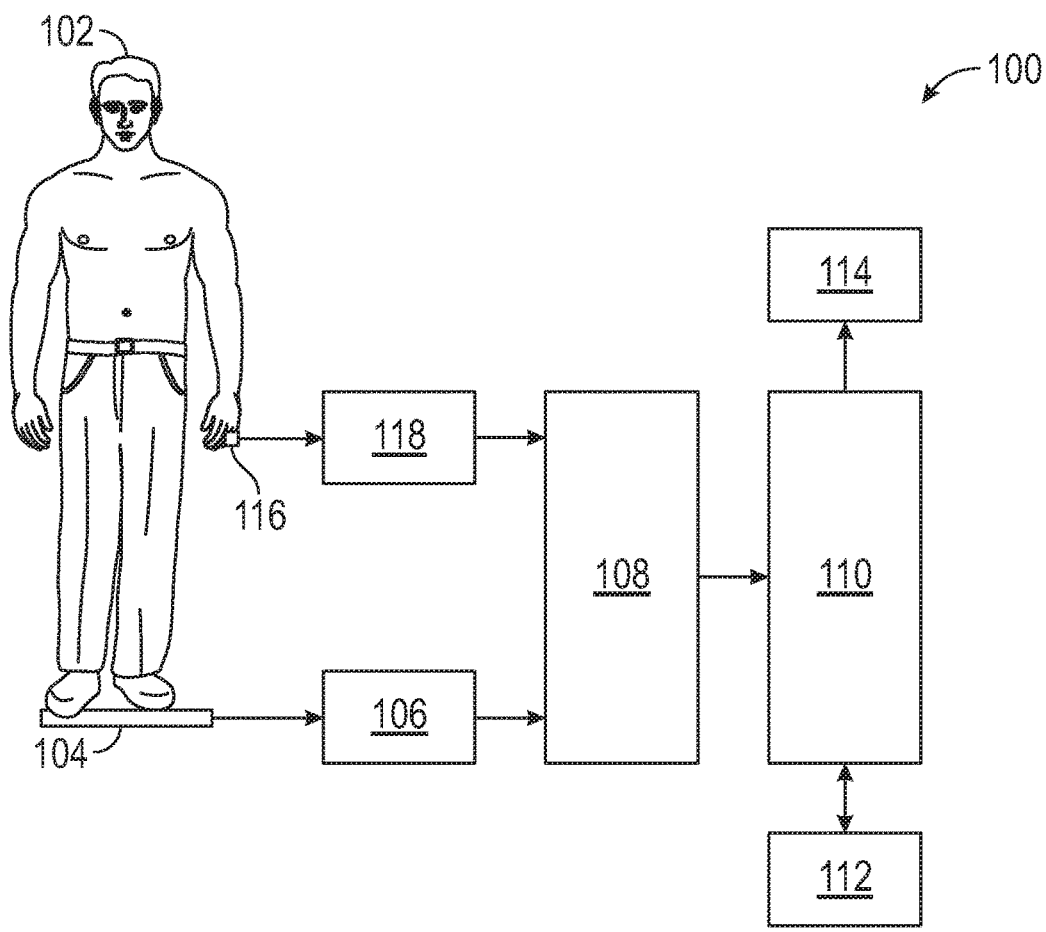
FIG. 1 is a diagrammatic representation of a system for monitoring arterial properties, such as blood pressure, in accordance with various representative embodiments of the disclosure.

The various methods, systems, apparatuses, and devices described herein can generally provide for the monitoring arterial properties such as systolic and diastolic pressure levels.

For example, in accordance with certain representative embodiments of the present disclosure, there is provided a method and apparatus for determining arterial properties from ballistocardiogram data alone, or from a combination of ballistocardiogram data and other cardiac measurements, such blood pressure levels.

While implementations of the disclosure are susceptible to embodiment in many different forms, there is shown in the drawings and will herein be described in detail specific embodiments, with the understanding that the present disclosure is to be considered as an example of the principles of the disclosure and not intended to limit the disclosure to the specific embodiments shown and described. In the description below, like reference numerals are used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including," "has," "having," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment", "certain embodiments", "an embodiment," "implementation(s)," "aspect(s)," or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

All documents mentioned herein are hereby incorporated by reference in their entirety. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," "above," "below," and the like, are words of convenience and are not to be construed as limiting terms. Also, the terms apparatus and device may be used interchangeably in this text.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

As used herein, the term processor, controller or the like may encompass a processor, controller, microcontroller unit (MCU), microprocessor, and other suitable control elements. It will be appreciated that embodiments of the disclosure described herein may be comprised of one or more conventional processors and unique stored program instructions that control the one or more processors to implement, in conjunction with certain non-processor circuits, some, most, or all of the functions described herein. The non-processor circuits may include, but are not limited to, a receiver, a transmitter, a radio, signal drivers, clock circuits, power source circuits, and user input devices. As such, these functions may be interpreted as a method to perform functions in accordance with certain embodiments consistent with the present disclosure. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

One aspect of the present disclosure is a method for analyzing ballistocardiogram (BCG) signals to detect and monitor cardiac health and diseases. The method includes determining arterial pressure gradient information from BCG signals, measuring BCG and blood pressure waveforms, deriving further parameters, and utilizing the results and method to detect any abnormalities in proximal and distal arteries. The method can be used as a non-intrusive tool for assessing and screening diseases in the heart and arteries.

Ballistocardiogram (BCG) is the recording of the cardiac force caused by the ejection of blood by the heart. The blood pressure (BP) and flow formed by the blood ejection act on the blood to accelerate and decelerate the blood, which in turn moves the body as reaction. Thus, BCG is related to BP and flow. Therefore, it is possible to extract a great deal of information relevant to the health and disease associated with the heart and the arteries by analyzing the BCG.

Previously, the BCG has been interpreted as a measure of ballistic forces on the heart and the mechanical movement of the heart. The BCG has been used as a vital sign in that some heart malfunctions can be identified by observing and analyzing the BCG signal, but the BCG has not been used to monitor blood pressures, and more generally, the BCG has not been used for unobtrusive monitoring and diagnosis of cardiovascular health and disease.

It is disclosed that the systemic arterial BP gradients are the primary mechanism underlying the genesis of the BCG. Consequently, an analysis of the BCG waveform can provide critical insights as to the underlying systemic arterial BP. To analyze the BCG waveform in a systematic and objective manner, a mathematical model can be used that relates the BCG to systemic arterial BP and flow. When the BCG and aortic blood pressure waveforms are measured, the model may be fitted to the BCG and blood pressure data to derive the parameters in the model that are useful for detecting and diagnosing the diseases in the heart and the vasculature.

The aforementioned model, once fitted to derive its parameters, may exhibit pulse wave velocity and arterial wave reflection characteristics that are often closely related to vascular diseases including, but not limited to, abdominal aortic aneurysms (AAA), peripheral vascular stenosis and arterial stiffening. Thus, the use of the model together with the BCG and an arterial circulatory waveform measurement enables low-cost screening of vascular disease.

Various embodiments of the present disclosure relate to a method and apparatus for sensing systolic and diastolic pressure of a subject. An embodiment of the method comprises collecting BCG data of the subject, where the BCG data comprises a waveform having 'I', 'J' and 'K' peaks, computing, by a hardware processor, a blood pulse pressure (PP) from an amplitude difference between the 'J' and 'K' peaks of the waveform, computing, by the hardware processor, the diastolic pressure from a time interval between the 'I' and 'J' peaks of the waveform; and estimating the systolic pressure by adding the diastolic pressure to the pulse pressure. Herein, the term 'peak' is used to refer to a local extremum of the waveform, which may be a maximum or a minimum.

The method may utilize a discovery of a previously unknown mechanism that is responsible for the production of the BCG waves. BCG waves result from interaction between the aortic blood pressure (BP) waves. In particular, BCG waves are generated by a combination of blood pressure differences across the ascending aorta (formed by the aortic inlet and arch BP waves) and blood pressure differences across the descending aorta (formed by the aortic arch and outlet BP waves). These pressures difference are referred to herein as pressure gradients.

Herein, the blood pressure at the aortic inlet, aortic arch and aortic outlet at time t are denoted by $P_0(t)$, $P_1(t)$ and $P_2(t)$, respectively.

The 'J' peak in the BCG data amplitude occurs when the pressure difference across the ascending aorta of the subject is relatively small, but the pressure difference across the descending aorta of the subject is relatively large, since the pressure at the proximal end of the descending aorta is at the systolic level while pressure at the distal end of the descending aorta is still at the diastolic level. The 'K' peak in the BCG data occurs when the blood pressure at both proximal and distal ends of the descending aorta of the subject reaches the systolic level. The amplitude difference between the and 'K peaks is therefore related to the pulse pressure.

The method may also recognize that the time interval between an 'I' peak and a peak in the ballistocardiogram data relates to a pressure pulse transit time (PTT) in the descending aorta, which, in turn, is related to the diastolic pressure.

The physical insight obtained from the discovery of a physical mechanism behind BCG force yields at least two morphological features in the BCG waveform that may be used to provide ultra-convenient cuff-less BP monitoring that was previously unavailable and unobtainable in manners disclosed herein. First, it is noted that the onsets of aortic inlet and outlet BP waves approximately correspond to the initiation of the first major wave (called the 'I' wave) and the peak of the second major wave (called the 'J' wave) in the BCG, respectively. The time interval between the initiation of the 'I' wave and the peak of the 'J' wave (called the "I-J interval" hereafter) thus approximately represents aortic PTT, a well-known surrogate of diastolic pressure (DP). Second, it is noted that the aortic inlet and arch BP waves remain at the systolic level while the aortic outlet BP wave increases from its diastolic to systolic level (i.e., by pulse pressure (PP)) during the down-stroke from the T wave to the third major wave in the BCG (called the 'K' wave). The amplitude between the peaks of the J and K waves (called the "J-K amplitude" hereafter) thus approximately represents aortic outlet (which may correspond to a site near the femoral artery) PP.

In one embodiment, the BCG I-J interval and J-K amplitude are used to monitor BP (in particular, DP and SP independently), either in conjunction with PTT or based on the BCG alone, without the use of an inflatable cuff. The I-J interval is used as a surrogate for diastolic pressure (DP) and J-K amplitude is used as a surrogate for pulse pressure (PP). Previously, PP was only available through the use of cuff-based or intrusive monitoring. In addition, previously, a single PTT was used to monitor both DP and SP.

FIG. 1 is a diagrammatic representation of a system 100 for monitoring arterial properties, such as blood pressure, in accordance with various representative embodiments of the disclosure. System 100 monitors arterial properties of a subject 102. System 100 includes a sensor 104 configured to provide BCG data in response to cardiac forces acting on subject 102 in at least the head-to-foot direction, where the BCG data comprises a waveform having 'I', 'J' and 'K' peaks. Thus, sensor 104 may include a motion sensor configured to sense cardiac forces acting on the subject 102. In one embodiment, whole body motion sensor 104 comprises a high-resolution force plate such as force plate model number 9260AA6 manufactured by Kystler Group, Wintetthur, Switzerland. Sensor 104 may thus include a force plate. Sensor 104 may also or instead include other sensing devices such as an acceleration, velocity, or displacement sensor. Sensor 104 may also or instead include body-mountable devices configured to sense whole-body motion in response to cardiac force, such as where whole-body motion is sensed by an accelerometer in response to cardiac forces. Sensor 104 may be provided in certain objects such as a bed, a chair, and so on, e.g., for ease of use in different settings and environments. Sensor 104 may be configured to measure at least the head-to-foot force on the subject. Sensor 104 may, in addition, measure forces in other directions to compensate for variation in the posture of subject 102, for example. Other whole-body sensors may be used, such as an in-ear motion sensor or commercial weighing scale. Sensor 104 provides a force signal to signal conditioning unit 106 that, in turn, provides a conditioned signal to data acquisition unit 108.

Data acquisition unit 108 is configured to sample and digitize the conditioned signal and provide it to a hardware processor 110, e.g., a hardware processor 110 configured to receive BCG data. Hardware processor 110 is operatively coupled to a storage system 112 that is used to store data and computer instructions. In particular, storage system 112 may include a non-transient computer readable medium for storing computer instructions for controlling the hardware processor 110. Storage system 112 may also be used to store monitored arterial properties. Storage system 112 may also or instead be configured to store calibration data that is used in determining the pulse pressure level from an amplitude difference between the 'J' and 'K' peaks of the waveform. Storage system 112 may also or instead be configured to store calibration data that is used in determining the diastolic pressure level from a time interval between the 'I' and 'J' peaks of the waveform. Hardware processor 110 is operatively coupled to a user interface 114. User interface 114 may include, for example, a visual display unit to display monitored arterial properties, such as blood pressures (e.g., to display the systolic and diastolic pressure levels). Hardware processor 110 may be located in proximity to sensor 104 or at a remote location. Hardware processor 110 may be configured to communicate with sensor 104 via a wired or wireless network.

Thus, the system 100 may include a non-transient computer readable medium accessible by the hardware processor 110 and containing instructions that, when executed by the hardware processor, performs a sensing of systolic and diastolic pressure levels of the subject 102, and/or analysis of BCG data for blood pressure monitoring or the like. In certain implementations, a non-transient computer readable medium (e.g., the storage system 112) accessible by the hardware processor 110 contains instructions that, when executed by the hardware processor 110, performs a method comprising determining the diastolic pressure level from a time interval between the 'I' and 'J' peaks of the waveform, determining the diastolic pressure level from a time interval between the 'I' and 'J' peaks of the waveform, and determining the systolic pressure level from the time interval between the 'I' and 'J' peaks of the waveform and the amplitude difference between the T and 'K' peaks of the waveform, where the systolic and diastolic pressure levels are provided as outputs from system 100. The instructions, when executed by the hardware processor 110, may further determine a pulse pressure level from the amplitude difference between the 'J' and 'K' peaks of the waveform, where the systolic pressure level is determined from the pulse pressure level and the diastolic pressure level.

Also, or instead, in one embodiment, instructions stored in the non-transient computer readable medium of storage system 112, when executed by the hardware processor 110, perform a method comprising computing a pulse pressure from an amplitude difference between the 'J' and 'K' peaks of the waveform, computing a diastolic pressure from a time interval between the 'I' and 'J' peaks of the waveform, and estimating the systolic pressure by adding the diastolic pressure to the pulse pressure. In addition, the instructions may cause the resulting blood pressures to be stored in storage system 112, displayed on user interface 114, or transmitted to a remote location via a network, for example.

The relationship between blood pressure and BCG data is dependent upon a variety of properties, including the sensitivity of the sensing system, transmission of aortic forces through the body of the subject, and properties of the subject's aorta. Using the relationship between the features extracted from the BCG waveform and the blood pressure, other arterial properties may be obtained via calibration. The calibration may be performed for a particular subject, for a group of subjects (such as subjects within a weight range, age range, height range, gender group, etc.), or for all subjects. When a weight range is used, for example, sensor 104 (e.g., a force plate) may sense the subject's weight and processor 110 may select the corresponding calibration data dependent upon the sensed weight. The calibration may be performed using a cuff-based blood pressure monitor such as a cuff 116—e.g., an arm cuff, a wrist cuff or, as shown in FIG. 1, a finger cuff. The cuff-based BP signal may be conditioned in signal conditioning unit 118 and passed to data acquisition unit 108. Alternatively, cuff-based monitor may provide a digital signal to hardware processor 110 or calibration levels may be entered via user interface 114. Once system 100 is calibrated, blood pressure may be determined from the BCG waveform alone. The calibration may use a sensor, such as an inflatable cuff, to measure arterial volume waveforms or blood pressure waveforms. This waveform data may be compared with the BCG waveform to estimate parameters in a BCG model. A variety of techniques for identifying the relationship between the measured blood pressure and BCG data will be apparent to those of ordinary skill in the art.

It will be understood that the system 100 shown in FIG. 1 may be included in a standalone device containing all components of the system 100 (apart from the subject 102), or in multiple devices. Thus, the components of the system 100 may be included in a single blood pressure monitor in an embodiment of the present teachings. This blood pressure monitor may be used for sensing systolic and diastolic pressure levels of the subject 102.

Figure 2:
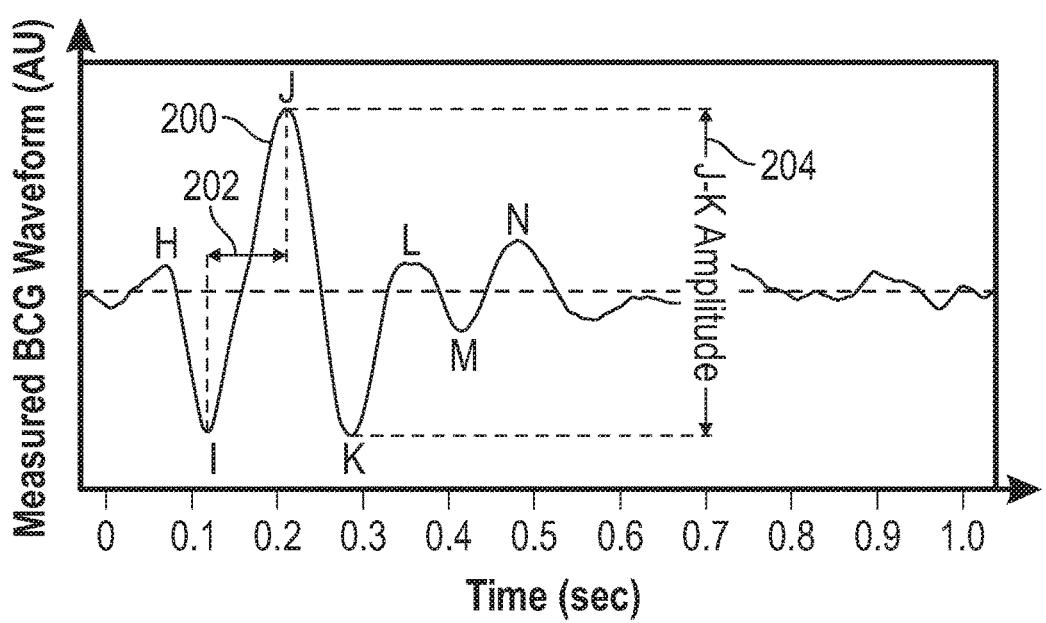
FIG. 2 is a graph of an exemplary ballistocardiogram (BCG) waveform over one cardiac cycle.

FIG. 2 is a graph of an exemplary BCG waveform over one cardiac cycle. The waveform 200 is indicative of head-to-foot forces acting on a subject due to blood pressure fluctuations, and exhibits a number of extrema denoted by the letters 'H' to 'N'. As discussed above, time interval 202 is referred as the I-J interval and is related to a pulse transit time (PTT) of a blood pressure pulse transiting the aorta of the subject. Amplitude 204 is referred to as the J-K amplitude and, as discussed above, is related to the pulse pressure (PP).

It has long been known that the body recoils each time the heart ejects blood into the arteries. These subtle cardiogenic body movements have been measured with increasingly convenient BCG instruments over the years. As shown in FIG. 2, above, a typical BCG measurement shows several waves, most notably the 'I', 'J', and 'K' waves. The mechanism for the genesis of these BCG waves was not known previously, but a mathematical model of the genesis of the BCG waveform is disclosed below. The applicant has demonstrated that the model can predict the BCG waveform in addition to the physiologic timings and amplitudes of the major waves. The validated model reveals that the whole-body forces that give rise to the BCG waves are the result of blood pressure gradients in the ascending and descending aorta. This newly discovered mechanistic insights can facilitate an understanding of the methods and apparatus disclosed herein. For example, based on an understanding that a mechanism for the genesis of the BCG waves is blood pressure gradients in the ascending and descending aorta, BCG data can be used for previously unavailable unobtrusive monitoring and diagnosis of cardiovascular health and disease.

Various BCG instruments have been developed (ranging from tables to wearable devices) to measure the periodic, reactionary forces experienced by the body. FIG. 2 illustrates an example of a measured BCG waveform for one heartbeat. The example shows several waves such as the 'I', 'J', and 'K' waves, which are typical of BCG recordings. Prior understanding of the BCG waves is based mainly upon empirical correlations with other measurements such as the electrocardiogram, phonocardiogram, and blood pressure (BP) waveform. However, theoretical efforts to explain the underlying mechanism have been relatively rare. Further, while a few mathematical models of the BCG waveform have been proposed, these models have either failed to reproduce the key BCG waves or were too complicated to glean any mechanistic insight. Hence, despite increasing interest in BCG, the origin of the BCG waves has not been understood. In particular, the BCG was thought to relate to mechanical forces on the heart rather than to aortic pressure gradients. As such, the BCG was not considered as tool for blood pressure monitoring.

A Model of the BCG Waveform

The instantaneous force on a subject in the head-to-foot direction is denoted as $F_{BCG}(t)$. Generation of the BCG waveform may be modeled, mathematically, by analyzing the equilibrium of forces exerted on the blood in the main artery of the body, the aorta. In a simple form of the model, the force at time t is approximated by:

$$F_{BCG}(t) \approx A_D[P_1(t)-P_2(t)]-A_A[P_0(t)-P_1(t)] = A_D\delta P_{12}(t) - A_A \delta P_{01}(t) \quad (1)$$

Here, $A_A$ and $A_D$ represent the average cross-sectional areas of the ascending and descending aorta. As mentioned above, $P_0(t)$ represents BP at the inlet of the ascending aorta; $P_1(t)$ represents BP at the outlet of the ascending aorta or inlet of the descending aorta; and $P_2(t)$ represents BP at the outlet of the descending aorta. Note that $\delta P_{01}(t)=P_0(t)-P_1(t)$ and $\delta P_{12}(t)=P_1(t)-P_2(t)$ constitute the BP differences or gradients in the ascending and descending aorta. Thus, this model predicts that the principal mechanism for the genesis of the BCG waves is BP gradients in the ascending and descending aorta. Derivation of this expression is discussed below with reference to FIG. 3.

The practical use of equation (1) to derive cardiovascular parameters may require the knowledge (e.g., measurement) of at least 3 BPs. However, $P_0(t)$ and $P_1(t)$ can be expressed in terms of $P_2(t)$ using the following transmission line relationships in the Laplace transform domain:

$$P_2(s) = \frac{1+\Gamma(s)}{e^{\tau_i s} + e^{-\tau_i s}\Gamma(s)} P_i(s), i = 0, 1 \quad (2)$$

where s is a Laplace transform variable.

Writing $$R_i = \frac{e^{\tau_i s} + e^{-\tau_i s}\Gamma(s)}{1+\Gamma(s)},$$

the BCG force can then be written in terms of $P_2(t)$ alone as:

$$F_{BCG}(s) = A_D(R_1-1)P_2(s) - A_A(R_0-R_1)P_2(s) \quad (3)$$

where $\tau_0$ and $\tau_1$ are pressure pulse transit times and F(s) is a reflection coefficient at the distal end of the descending aorta of the subject. In contrast to equation (1), equation (3) may require knowledge of only one BP. While equations (1) and (3) are forms of the same model, equation (3) may be more advantageous in practical cardio-vascular (CV) health monitoring. Thus, equation (3) may enable more convenient and practical approaches to CV parameter estimation from a BCG and an arterial waveform.

It is noted that equation (2) is an approximation. It will be apparent to those of ordinary skill in the art that a more detailed expression may be used to take account of other reflection coefficients, arterial wall stiffness, etc. For example, the model may take into account the reflection coefficients at a distal end of the ascending aorta of the subject.

Figure 3:
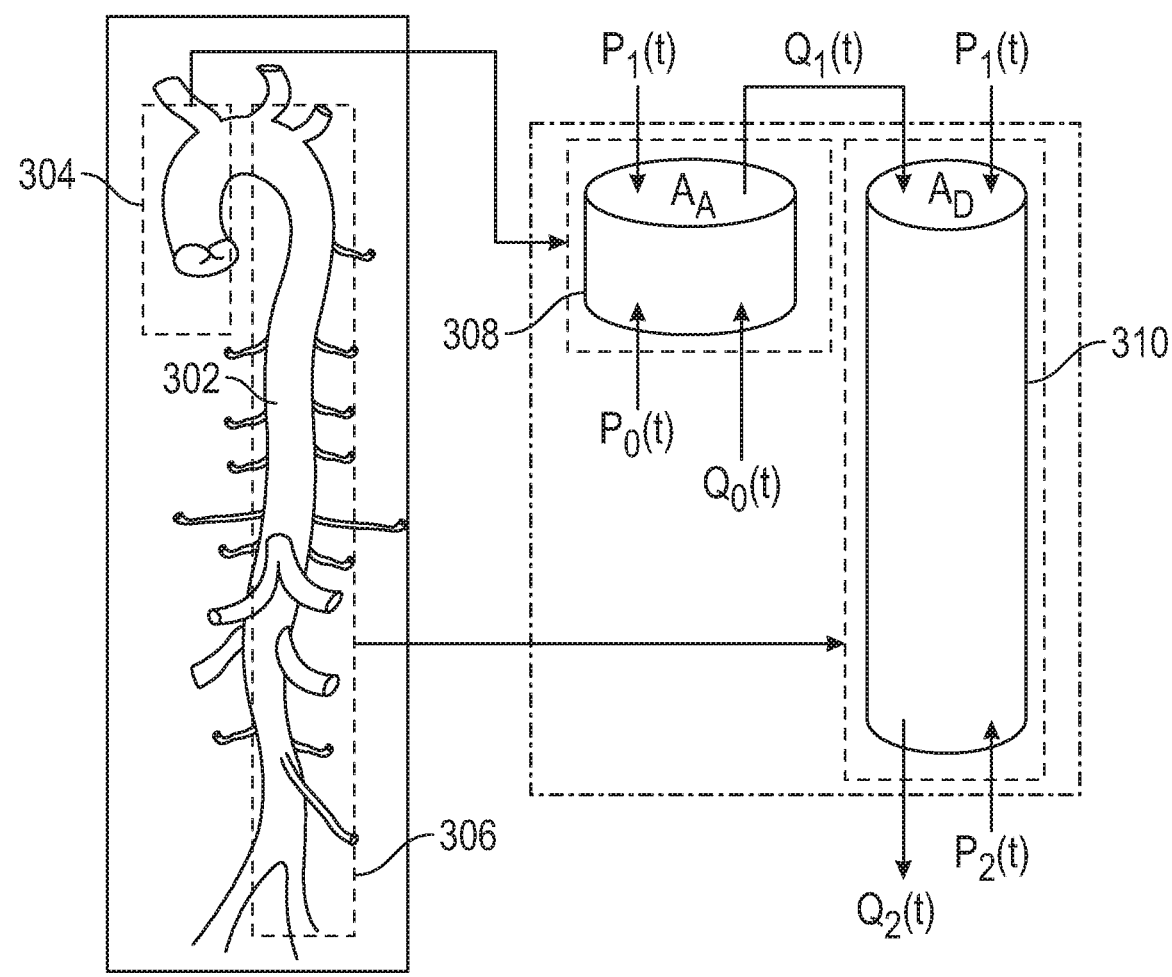
FIG. 3 is a diagrammatic representation of an aorta together with a model of BCG forces, in accordance with various representative embodiments of the disclosure.

FIG. 3 is a diagrammatic representation of an aorta 302. Aorta 302 comprises an ascending part 304 and a descending part 306. In the model, the ascending part 304 of the aorta 302 is approximated as a short tube 308 (representing the ascending aorta wherein blood moves in the head-ward direction) and the descending part 306 of the aorta 302 is approximated as a long tube 310 (representing the descending aorta wherein blood moves in the foot-ward direction) connected in cascade. The ascending tube 308 is subject to BP and volume flow rate waveforms at the inlet of the aorta ($P_0$ (t) and $Q_0$ (t)) and apex of the aortic arch ((t) and $Q_1$(t)), while the long tube 310 (descending tube) is subject to $P_1$ (t) and $Q_1$(t) as well as the BP and volume flow rate waveforms at the outlet of the aorta ($P_2$ (t) and $Q_2$ (t)). It is noted that, because of pressure wave transmission and reflection in the arteries, all of these waveforms differ in terms of timing, amplitude, and shape.

The forces acting on the blood in the tubes may be approximated by considering the blood in each tube to be a control volume and by making the following simplifying assumptions: (i) blood is homogenous and incompressible; (ii) the cross-sectional area of tube changes little (i.e., the arterial wall is stiff and geometric tapering is small); and (iii) blood flow is longitudinal with uniform velocity profile (i.e., inviscid flow). These assumptions are generally well justified based on experimental data. Hence, according to Newton's second law, the force acting on blood in each tube (F(t)) is due to the BP waveforms at its inlet and outlet, which change the blood velocity in the tube, and the volume flow rate waveforms at its inlet and outlet, which change the blood mass in the tube, as follows:

$$F_A(t) = \left[P_0(t)A_A + \frac{\rho Q_0^2(t)}{A_A}\right] - \left[P_1(t)A_A + \frac{\rho Q_1^2(t)}{A_A}\right] \quad (4)$$

$$F_D(t) = \left[P_2(t)A_D + \frac{\rho Q_2^2(t)}{A_D}\right] - \left[P_1(t)A_D + \frac{\rho Q_1^2(t)}{A_D}\right]$$

where $\rho$ is blood density (which is near that of water), while the subscripts A and D denote the ascending and descending tubes, respectively. Note that a hydrostatic term ($\rho gh$, where g is gravity and h is the vertical distance of the aortic inlet or outlet relative to the heart) could be readily added to the BP terms in this equation when needed (e.g., BCG measurement in standing rather than supine posture). The BCG waveform ($F_{BCG}(t)$) is modeled as the sum of the forces in both tubes but in opposite direction in accordance with Newton's third law as follows:

$$F_{BCG}(t) = -[F_A(t) + F_D(t)] \quad (5)$$

$$= A_D\left[\left(P_1(t) + \rho\left[\frac{Q_1(t)}{A_D}\right]^2\right) - \left(P_2(t) + \rho\left[\frac{Q_2(t)}{A_D}\right]^2\right)\right] - A_A\left[\left(P_0(t) + \rho\left[\frac{Q_0(t)}{A_A}\right]^2\right) - \left(P_1(t) + \rho\left[\frac{Q_1(t)}{A_A}\right]^2\right)\right]$$

Comparing the relative magnitudes of the BP (P(t)) and velocity ($\rho[Q(t)/A]^2$) terms in this BCG model suggests that the contribution of the former is much larger than the latter. Indeed, typical aortic blood velocities are around 0.45-0.50 m/s, which yield $\rho[Q(t)/A]^2$ values of 1.6-1.9 mmHg, whereas BP is nominally around 100 mmHg. While aortic blood velocity can rise due to either a decrease in aortic cross-sectional area induced by atherosclerosis or an increase in cardiac output induced by exercise or otherwise, its contribution may still be quite small (e.g., <10%). The BCG model may therefore be simplified to equation (1).

Validity of the BCG Model

Validity of the mathematical model has been tested by analyzing invasive BP waveforms measured at the inlet and outlet of the aorta from cardiac surgery patients.

Figure 4:
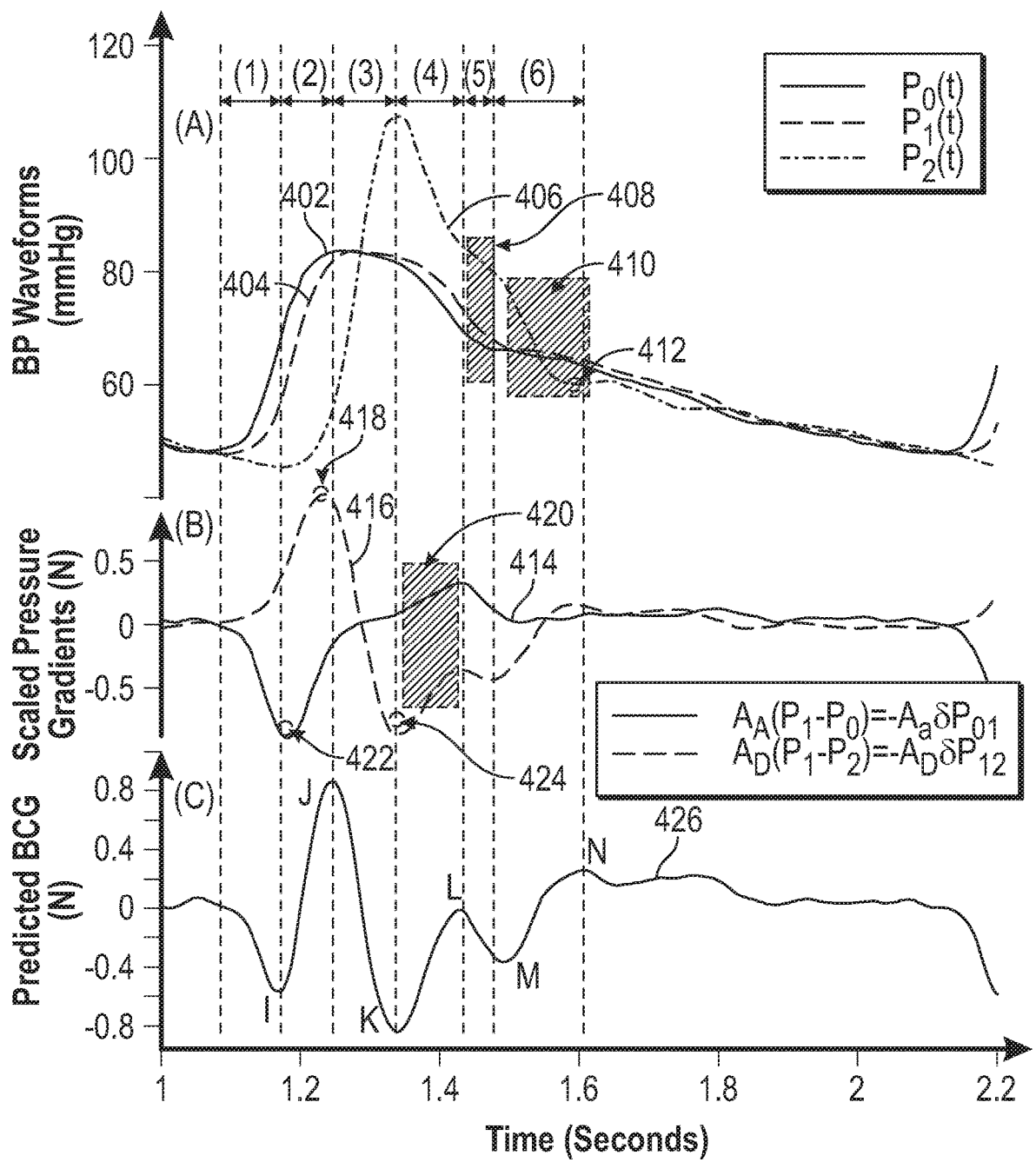
FIG. 4 shows an example of the blood pressure (BP) and BCG waveforms from a subject, in accordance with various representative embodiments of the disclosure.

FIG. 4 shows an example of the blood pressure (BP) waveforms from one patient. The $P_0(t)$, $P_1(t)$ and $P_2(t)$ BP waveforms are shown in the upper plot (A) in FIG. 4. $P_0(t)$ (shown as the solid curve 402) is the BP measured at the inlet of the ascending aorta; $P_1(t)$ (shown as the dashed curve 404) is the BP measured at the outlet of the ascending aorta or inlet of the descending aorta; and $P_2(t)$ (shown as the dash-dot curve 406) is the BP measured at the outlet of the descending aorta. In time period 408 in the upper plot, the pulse is reflected from the distal end of the aorta, and there is a superposition of forward and backward waves. In time 410, the distal pressure $P_2(t)$ is decreasing rapidly, so the pressure difference $P_1(t)-P_2(t)$ is increasing. At time 412, a notch occurs in $P_2(t)$.

The middle graph (B) of FIG. 4 shows the resulting BP gradients, scaled by the corresponding cross-sectional areas, when nominal values for the aortic cross-sectional areas, $A_A$ and $A_D$, were used. Solid line 414 shows the term $A_A[P_1(t)-P_0(t)]$, which corresponds to the force imparted by the pressures in the ascending aorta, while broken line 416 denotes the term $A_D[P_1(t)-P_2(t)]$ corresponding to the force imparted by pressures in the descending aorta. Portion 418 of broken line 416 represents a maximum of the scaled pressure difference $A_D[P_1(t)-P_2(t)]$ occurring. During the time period 420, distal pressures are decreasing faster than proximal pressures. The minimum in the scaled pressure difference $A_A[P_1(t)-P_0(t)]$ occurs at 422, while the minimum in the scaled pressure difference $A_D[P_1(t)-P_2(t)]$ occurs at 424.

The bottom graph (C) in FIG. 4 shows the BCG waveform 426 predicted for the patient. While the actual BCG was not measured concurrently, the predicted BCG waveform 426 has similar characteristics to BCG waveforms measured for other subjects. In particular, the model may consistently predict the presence of the major I, J, and K waves (e.g., for greater than 91% of the subjects) and even the minor L, M, and N waves (e.g., for greater that 83% of the patients). Further, as shown in TABLE 1 below, the model can predict physiologic timings and amplitudes for the major waves.

The top row of TABLE 1 (labeled as 'Model') shows mean values and +/−standard deviations for the timings and amplitudes of the predicted BCG waves for 21 subjects. For comparison, the middle and bottom rows (labeled as 'Set 1' and 'Set 2') show mean values for measured timings and amplitudes reported in the literature.

TABLE 1

| | Timings | | | Amplitudes | |
|---|---|---|---|---|---|
| | I-J Interval (ms) | J-K Interval (ms) | I-K Interval (ms) | I-IJ Ratio (%) | JK-IJ Ratio (%) |
| Model | 68 ± 11 | 91 ± 28 | 158 ± 35 | 48 ± 11 | 118 ± 38 |
| Set 1 | 72 | 89 | 161 | 50.8 | 129 |
| Set 2 | 75 | 88 | 163 | N/A | N/A |

Tests have indicated that the BCG waveform model is reasonably robust with respect to modest (e.g., ±10%) perturbations to the selected parameters used in the model, including the ratio of the aortic cross-sectional areas ($A_A/A_D$). In particular, the predicted BCG waveforms can exhibit the major I, J, and K waves in more than 91% of the patients for all different selected parameter settings. Further, alterations in the model-predicted timings and amplitudes of these waves may be small, with average absolute alterations of about 0.5% for the timings and about 5.5% for the amplitudes with respect to their nominal values.

The mechanism of the BCG waves, as described in the parametric model of equation (1), for the patient example in FIG. 4 is as follows. The initial build-up of the I wave is driven by $\delta P_{01}(t)$, as $P_0(t)$ starts to increase in systole while $P_1(t)$ is still in diastole (time period "(1)" in graphs (A), (B) and (C) of FIG. 4). The I wave peak occurs approximately when $\delta P_{01}(t)$ is maximal. As $P_1(t)$ starts to increase while $P_2(t)$ is still in diastole, $\delta P_{12}(t)$ builds up to cancel and then exceed $\delta P_{01}(t)$, thereby resulting in the I-J up-stroke (time period "(2)" in graphs (A), (B) and (C) of FIG. 4). The J wave peak occurs approximately when $\delta P_{12}(t)$ is maximal. As $P_2(t)$ builds up, $\delta P_{12}(t)$ decreases, and the J-K down-stroke occurs (time period "(3)" in graphs (A), (B) and (C) of FIG. 4). The K wave peak time occurs approximately when $P_2(t)$ is maximal or when $\delta P_{12}(t)$ is minimal. Right after the systolic peak, $P_2(t)$ decreases more quickly than $P_1(t)$ and results in an increase in $\delta P_{12}(t)$ ("(4)" in FIG. 3A-C). Meanwhile, $\delta P_{01}(t)$ exhibits a temporary decrease as $P_0(t)$ decreases fast near the dicrotic notch (time period "(4)" in graphs (A), (B) and (C) of FIG. 4). These events result in the L wave. Thereafter, $\delta P_{01}(t)$ increases to zero, while $\delta P_{12}(t)$ decreases slightly to a local minimum as $P_2(t)$ declines more slowly (time period "(5)" in graphs (A), (B) and (C) of FIG. 4). These events yield the M wave. The M-N up-stroke is related to the subsequent increase in $\delta P_{12}(t)$ due to the faster decrease in $P_2(t)$ (time period "(6)" in graphs (A), (B) and (C) of FIG. 4). Finally, the N wave peak approximately coincides with the time of the local maximum of $\delta P_{12}(t)$ caused by the diastolic notch appearing in $P_2(t)$.

Further Discussion

Based on the mechanism described above, the timings and amplitudes of the major I, J, and K waves can be viewed in terms of clinically significant cardiovascular parameters. First, the time of I wave initiation corresponds approximately to the trough or foot of the BP waveform at the inlet of the ascending aorta, while the time of the J wave peak corresponds approximately to the foot of the BP waveform at the outlet of the descending aorta (time periods "(1)" and "(2)" in FIG. 4). Hence, the time interval between the beginning of the I wave and peak of the J wave may represent the aortic pulse transit time, which is a powerful predictor of cardiovascular risk. Second, the amplitude of the J wave corresponds approximately to the aortic pulse pressure (PP=systolic BP−diastolic BP) scaled by the descending aortic cross-sectional area (end of time period "(2)" in FIG. 4). Since this area may change relatively little, the J wave amplitude may indicate relative changes in the aortic PP, which are often well correlated with relative changes in cardiac stroke volume. Third, the amplitude of the J-K down-stroke corresponds approximately to the peripheral PP scaled by the descending aortic cross-sectional area (time period "(3)" in FIG. 4). Hence, the ratio of the amplitude of the J-K down-stroke to the amplitude of the J wave may indicate PP amplification, which is another predictor of cardiovascular risk. While it is cautioned that the meaning of the wave features may strictly depend on the nature of the BP waveforms (e.g., time delays between waveforms) and aortic cross-sectional areas, the present teachings could be readily exploited to achieve effective, unobtrusive monitoring and diagnosis of cardiovascular health and disease, which was previously unavailable.

Example Method

Figure 5:
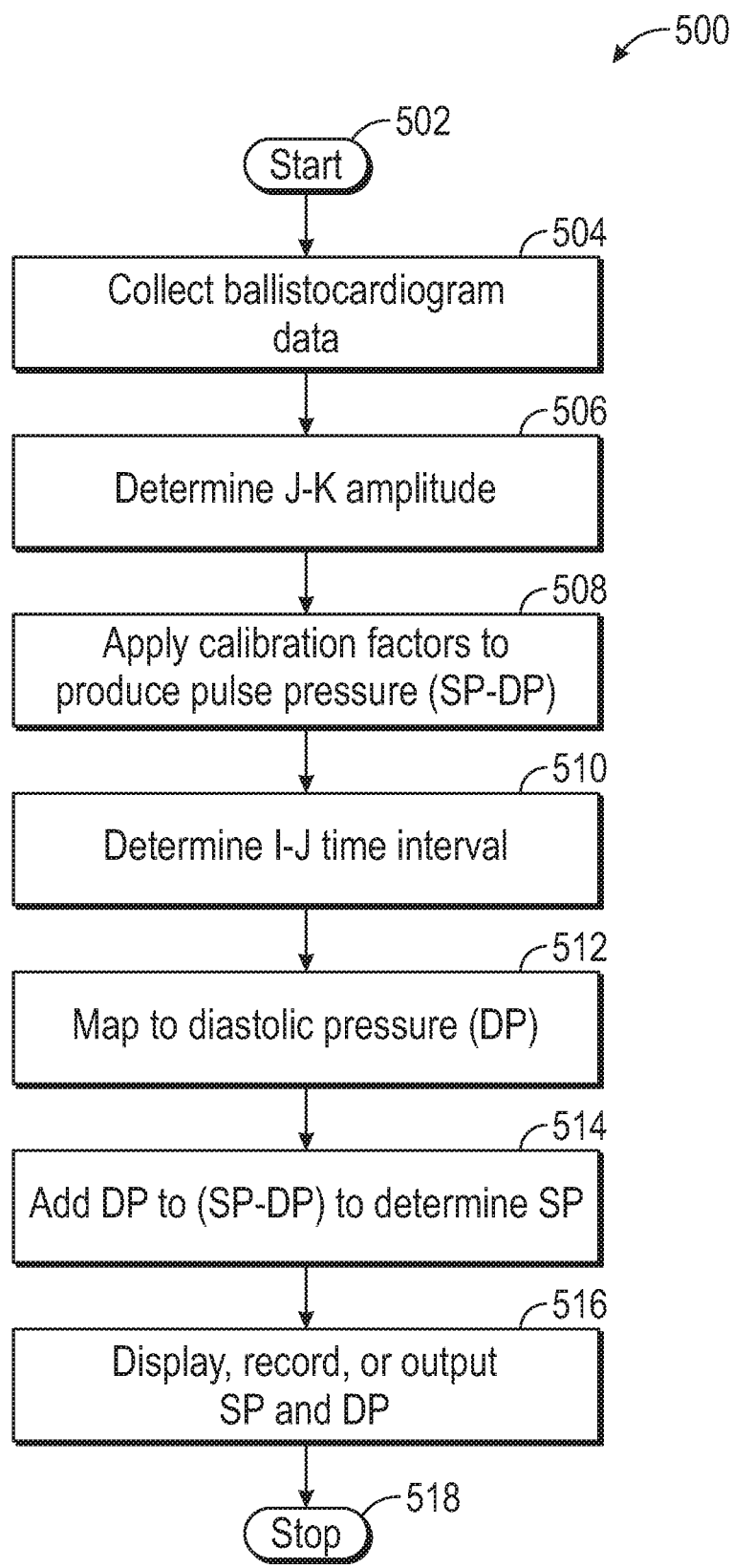
FIG. 5 is a flow chart of a method for monitoring BP using BCG data, in accordance with various representative embodiments of the disclosure.

FIG. 5 is a flow chart of a method 500 for monitoring blood pressure using BCG data. The method 500 may also or instead be used for sensing one or more arterial properties of a subject. Following start block 502 in FIG. 5, BCG data is collected at block 504. Thus, block 504 may include collecting BCG data of the subject for one or more cardiac cycles. The method 500 may further include detecting a 'J' peak in the BCG data, and detecting a 'K' peak in the BCG data. The J-K amplitude may be determined at block 506 by measuring the difference in amplitude between the 'J' peak and the 'K' trough of the BCG waveform. Stated otherwise, the method 500 may include determining an amplitude difference between the T peak and the 'K' peak. Using this determination, the method 500 may include determining a pulse pressure level from the determined amplitude difference, where one or more arterial properties sensed in the method 500 include the determined pulse pressure level. Further, or instead, a calibration factor may be applied at block 508 to compensate for properties of the aorta (such as ascending and descending aortic cross-sectional areas) and other factors such as the sensitivity of the ballistocardiograph and the force transmission path from the aorta to the ballistocardiograph. These factors may be lumped together as a single calibration factor. The calibrated level corresponds to a pulse pressure level, i.e. the difference, PP=SP-DP, between the systolic pressure level (SP) and the diastolic pressure level (DP). At block 510 the I-J time interval is measured. The I-J interval corresponds to a pulse transit time (PTT). Thus, the method 500 may include determining a PTT by detecting a time interval between an 'I' peak and al' peak in the BCG data, where one or more arterial properties sensed in the method 500 include the PTT. Further, or instead, a calibration factor may be applied at block 512 to map the PTT to a diastolic pressure level (DP). Thus, the method 500 may include determining a diastolic pressure level from the PTT. The diastolic pulse pressure level DP may be added to the pulse pressure level PP to provide a measure of the systolic pressure level (SP) at block 514. In this manner, one or more arterial properties sensed in the method 500 include the DP and the SP. The SP and DP levels may be displayed, recorded, or they may be provided as output at block 516, where the method may terminate at block 518.

In the method 500, collecting the BCG data may include sensing cardiac forces acting on the subject in at least a head-to-foot direction to provide a first signal, sensing cardiac forces acting on the subject in at least a head-to-foot direction to provide a first signal, and providing the sequence of sampled values to a hardware processor or the like. Further, sensing cardiac forces acting on the subject may include sensing acceleration, velocity, or displacement data of the subject. As discussed above, the one or more arterial properties sensed by the method 500 may be displayed at a user interface in communication with the hardware processor.

Instead of, or in addition to, the method 500 described above, the present teachings may include sensing systolic and diastolic pressure levels of a subject. In this manner, certain implementations may include sensing BCG data of the subject including a waveform having 'I', 'J' and 'K' peaks, determining (e.g., by a hardware processor) a pulse pressure level from an amplitude difference between the 'J' and 'K' peaks of the waveform, determining (e.g., by a hardware processor) the diastolic pressure level from a time interval between the 'I' and 'J' peaks of the waveform, and determining (e.g., by a hardware processor) the systolic pressure level by adding the diastolic pressure to the pulse pressure.

Similarly, certain implementations may include an apparatus for sensing arterial properties of a subject, where the apparatus includes a sensor configured to provide measured BCG data in response to at least head-to-foot cardiac forces acting on of the subject (e.g., such as sensor 104 described above), a blood pressure sensor configured to provide blood pressure level data (e.g., an inflatable cuff configured to measure systolic and diastolic pressure levels, an inflatable cuff configured to measure arterial volume waveforms, and the like), and a hardware processor configured for analyzing the sensed and measured data. For example, the hardware processor may be configured for receiving the BCG data and blood pressure level data, determining arterial parameters of a parametric model responsive to the blood pressure level data for which an output from the parametric model using the determined arterial parameters approximates the measured BCG data, and mapping the arterial parameters to the sensed arterial properties. The arterial parameters of the parametric model may include one or more of a cross-sectional area of an ascending aorta of the subject, a cross-sectional area of a descending aorta of the subject, a pulse transit time of the ascending aorta of the subject, a pulse transit time of the descending aorta of the subject, a reflection coefficient for a distal end of the ascending aorta of the subject, a reflection coefficient for a distal end of the descending aorta of the subject, and the like. Blood pressure level data may include a pulse pressure level, where the arterial parameters include a cross-sectional area of a descending aorta of the subject determined from the pulse pressure level and an amplitude difference between and 'K' peaks of the measured BCG data. The hardware processor of the apparatus may be further configured for detecting a presence or an absence of an abnormality by comparing the determined arterial parameters to a predetermined baseline parameter, and determining cardiac health of the subject, including a proclivity for a vascular disease, based on the presence or the absence of the abnormality. Determining arterial parameters of the parametric model may include setting estimated arterial parameters of the parametric model, and iteratively performing (i) executing the parametric model to provide estimated ballistocardiogram data and (ii) adjusting the estimated arterial parameters of the parametric model to reduce a difference between the estimated BCG data and the measured BCG data. The parametric model may give the estimated BCG data using equation (1) above.

Further, certain implementations may include an apparatus for monitoring systolic and diastolic pressure levels of a subject that includes a hardware processor configured to receive BCG data of the subject, where the BCG data comprises a waveform having 'I', 'J' and 'K' peaks. The apparatus may further include a non-transient computer readable medium accessible by the hardware processor and containing instructions that, when executed by the hardware processor, perform a method including determining a pulse pressure level from an amplitude difference between the 'J' and 'K' peaks of the waveform, determining a pulse pressure level from an amplitude difference between the 'J' and 'K' peaks of the waveform, and determining a pulse pressure level from an amplitude difference between the 'J' and 'K' peaks of the waveform. The systolic and diastolic pressure levels may be provided as apparatus outputs. The non-transient computer readable medium may be configured to store calibration data that is used in determining the pulse pressure level from the amplitude difference between the 'J' and 'K' peaks of the waveform and in determining the diastolic pressure level from the time interval between the 'I' and 'J' peaks of the waveform. The apparatus may further include a user interface configured to display the systolic and diastolic pressure levels.

Figure 6:
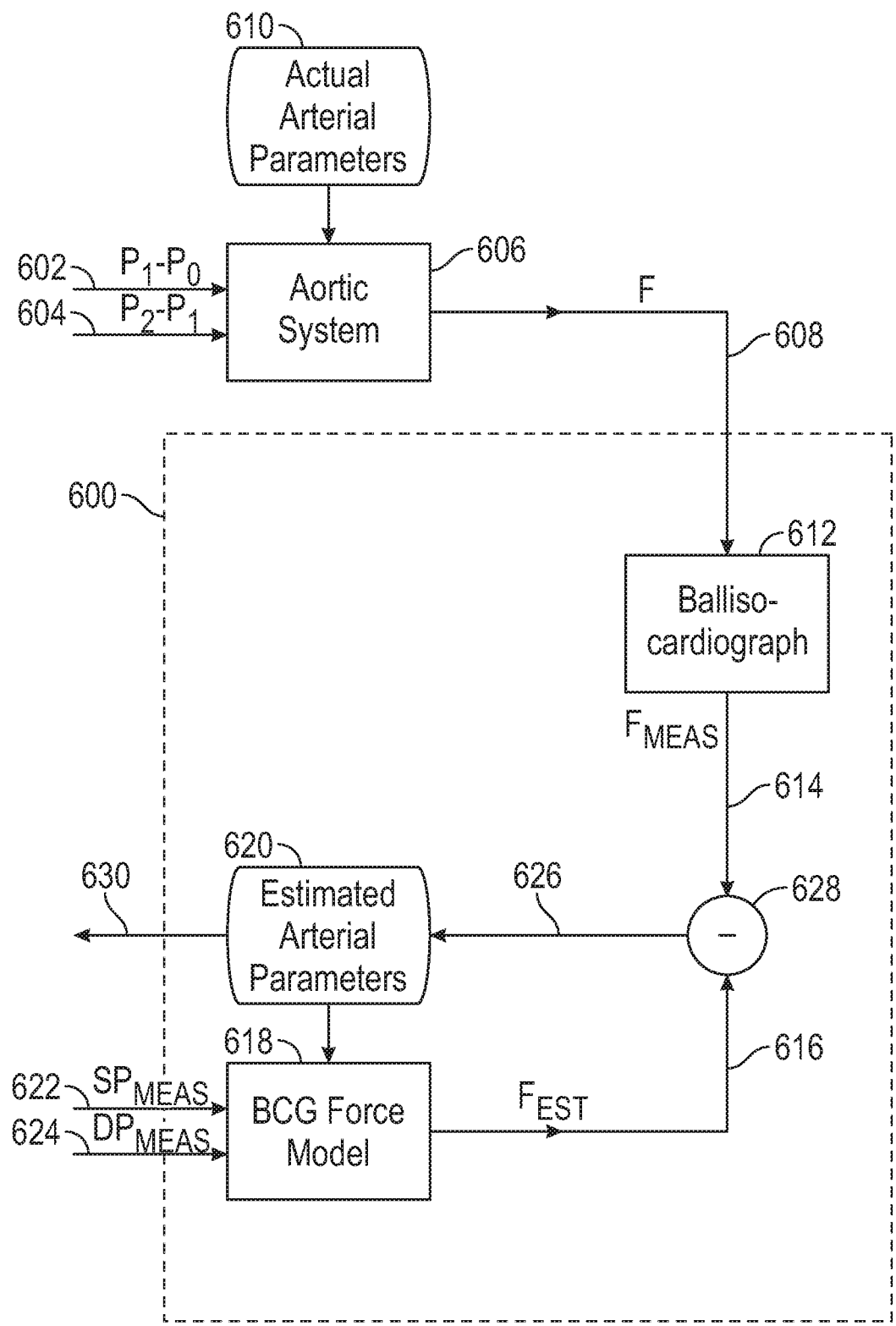
FIG. 6 is a block diagram of a system for measuring arterial parameters using BCG data, in accordance with various representative embodiments of the disclosure.

FIG. 6 is a block diagram of a system 600 for measuring arterial parameters using BCG data. Ballistocardiograph 612, 628, estimated arterial parameters 620 and BCG Force Model 618 comprise part of the system 600. In the body of a subject, pressure differences $P_1(t)-P_0(t)$ 602 and $P_2(t)-P_1(t)$ 604 across the ascending and descending aortas, respectively, react against the aortic system 606 to produce BCG forces F 608. The response of aortic system 606 depends upon a number of arterial parameters 610, such as aorta cross-sectional areas, wall stiffness, lengths, reflection coefficients, etc. The BCG forces F 608 are sensed by ballistocardiograph 612 to provide measured BCG data FMEAS 614. The estimated BCG force FEST 616, output from BCG model 618, is dependent upon estimated arterial parameters 620 and measured blood pressure levels, such as measured systolic pressure level 622 and measured diastolic pressure level 624. In a further embodiment, a blood pressure waveform or blood volume arterial waveform is input to BCG model 618. A difference 626 between the measured BCG forces FMEAS 614 and estimated BCG forces FEST 616 is determined in 628 and is used to adjust the estimated arterial parameters 620. Final estimated arterial parameters are output at 630. These arterial parameters may be used to calibrate a cuff-less blood pressure monitoring system, for example.

Figure 7:
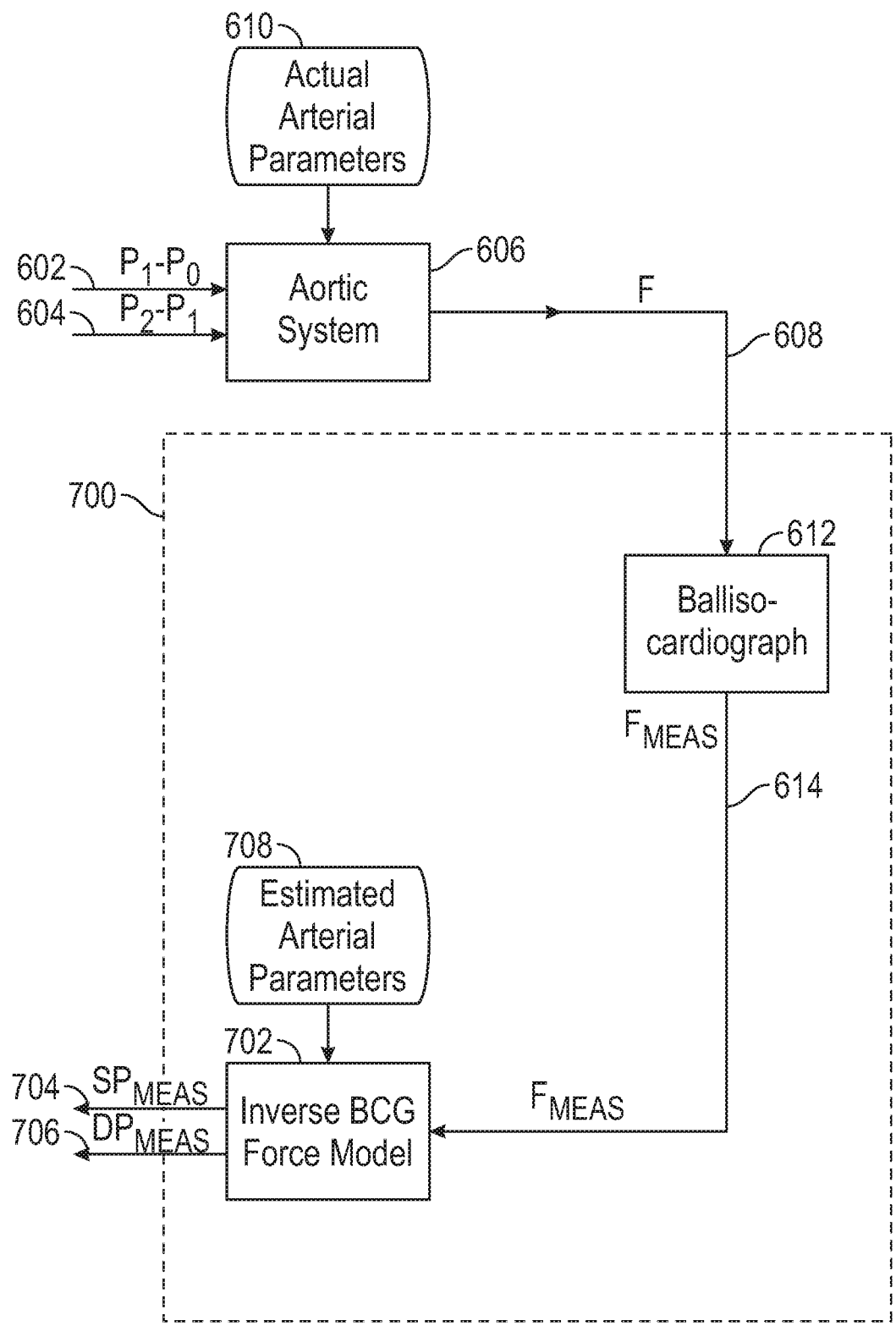
FIG. 7 is a block diagram of a system for monitoring blood pressure levels using BCG data, in accordance with various representative embodiments of the disclosure.

FIG. 7 is a block diagram of a system 700 for monitoring blood pressure levels using BCG data, in accordance with representative embodiments. As in FIG. 6, pressure differences $P_1(t)-P_0(t)$ 602 and $P_2(t)-P_1(t)$ 604 across the ascending and descending aortas, respectively BCG forces F 608 are sensed by ballistocardiograph 612 to provide measured BCG data FMEAS 614. However, in system 700 the measured BCG forces are processed in inverse BCG force model 702 to estimate systolic pressure level 704 and diastolic pressure level 706. Also shown are estimated arterial parameters FEST 708. Inverse BCG force model 702 uses arterial parameters 706 determined in a calibration phase, such as shown in FIG. 6. In contrast to prior systems, the system shown in FIG. 7 provides a cuff-less blood pressure monitor for both systolic and diastolic pressure levels.

It will be apparent to those of ordinary skill in the art that the art that, once the mechanism for BCG generation is identified, the relationship between blood pressures and arterial parameters may be used in a variety of ways to monitor the health of a subject.

While the method has been described in terms of the J-K amplitude and I-J interval extracted features, the blood pressure levels may be obtained by the extraction and mapping of other features of the BCG data. In one embodiment, for example, the features and mapping are obtained by training and then operating an artificial neural network or other machine learning system.

FIGS. 8A-8C and 9A-9C show graphs of experimental results showing the efficacy of using BCG to monitor blood pressure in a number of subjects. To analyze and compare the efficacy of the BP surrogates, each subject record was segmented into six periods: three baselines periods and three periods of physical interventions. In each period, the reference BPs and BP surrogates were averaged over five beat intervals. Then, the five-beat intervals where DP attained extremum (minimum for baseline periods and maximum for intervention periods) were identified. Next, six pairs of reference BPs-BP surrogates associated with DP extremum intervals were extracted from each of the 22 subject records for subsequent analysis.

The efficacy of the BP surrogates was analyzed and compared as follows. First, the correlation between the BP surrogates and the reference BPs was examined. In each subject, (1) the BCG PTT, pulse arrival time (PAT: time interval between the ECG R wave and the trough of finger PPG waveform), and the BCG I-J interval were calibrated to DP; and (2) the pairs of BCG PTT-BCG J-K amplitude and BCG I-J interval-BCG J-K amplitude as well as PAT were calibrated to SP. The calibration was performed using univariate and multivariate linear regression analysis. The correlation coefficients between the reference and calibrated BPs were then computed. Second, the root-mean-squared errors (RMSE) between the reference and calibrated BPs in each subject were computed as a measure of the best-case BP monitoring accuracy associated with each BP surrogate or surrogate pair. The correlation coefficients and RMSEs thus obtained were compared using the paired t-test as follows. First, BCG PTT, PAT, and BCG I-J interval in monitoring DP were compared. Second, BCG PTT, PAT, and the BCG PTT-BCG J-K amplitude pair in monitoring SP were compared. Third, BCG I-J interval, PAT, and the BCG I-J interval-BCG J-K amplitude pair in monitoring SP were compared. In all these comparisons, a significance level of p<0.016 was used after the Bonferroni correction factor of 3 (=0.3/5).

Figure 8A:
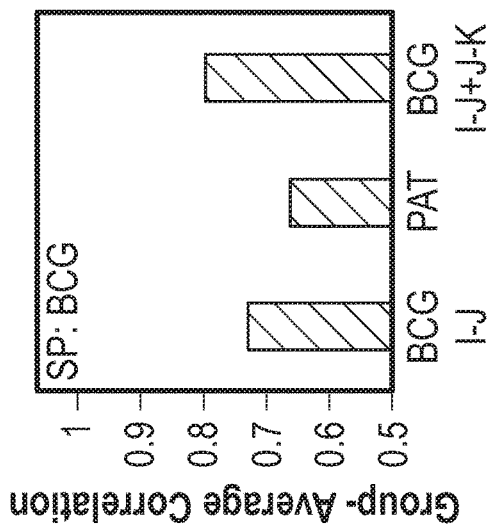
FIGS. 8A-8C show graphs of group average correlation coefficients between reference diastolic and systolic pressures (DP and SP) versus the corresponding surrogates, in accordance with various representative embodiments of the disclosure.
Figure 8B:
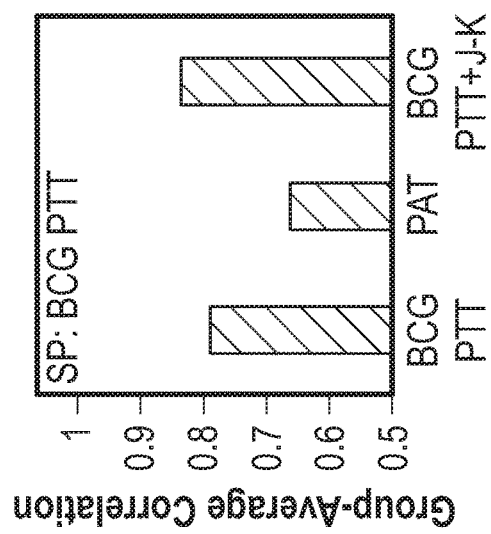
Figure 8C:
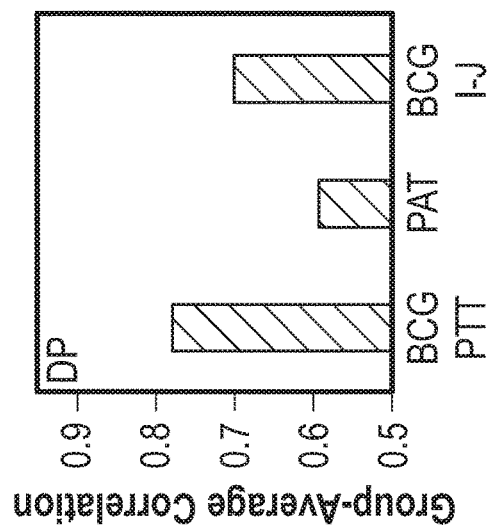

FIGS. 8A-8C show graphs of group average correlation coefficients (r values) between reference diastolic and systolic pressures (DP and SP) versus the corresponding surrogates for the six DP extremum intervals, in accordance with various representative embodiments of the disclosure.

FIG. 8A shows the correlations of the BCG PTT (first bar), PAT (second bar), and BCG I-J interval (third bar) with the DP. The correlation of the BCG I-J interval is comparable to that of the BCG PTT and PAT surrogates. The BCG I-J interval showed correlation coefficient for DP higher than PAT (by 19%) but lower than BCG PTT (by 11%).

FIG. 8B shows the correlations of the BCG PTT (first bar), PAT (second bar), and BCG PTT-BCG J-K amplitude pair (third bar) with the SP. The results show that the BCG PTT-BCG J-K amplitude pair was superior to both BCG PTT and PAT in monitoring SP. Multivariate linear regression of BCG PTT and BCG J-K amplitude pair to SP yielded higher correlation coefficients than BCG PTT (by 6%, with a significance level $p<0.005$) and PAT (by 26%; with a significance level $p<0.005$).

FIG. 8C shows the correlations of the BCG I-J interval (first bar), PAT (second bar), and BCG I-J interval and BCG J-K amplitude pair (third bar) with the SP. The results show the BCG I-J interval-BCG J-K amplitude pair was superior to BCG I-J interval alone and comparable to PAT in monitoring SP. Multivariate linear regression of BCG I-J interval and J-K amplitude to SP outperformed BCG I-J interval alone (by 9%; $p<0.015$) and PAT (by 20%).

Figure 9A:
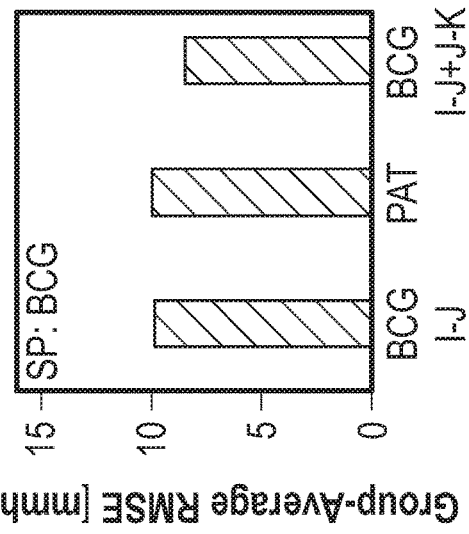
FIGS. 9A-9C show graphs of group average best-case root-mean-square (RMS) errors between reference DP and SP versus the corresponding calibrated DP surrogates, in accordance with various representative embodiments of the disclosure.
Figure 9B:
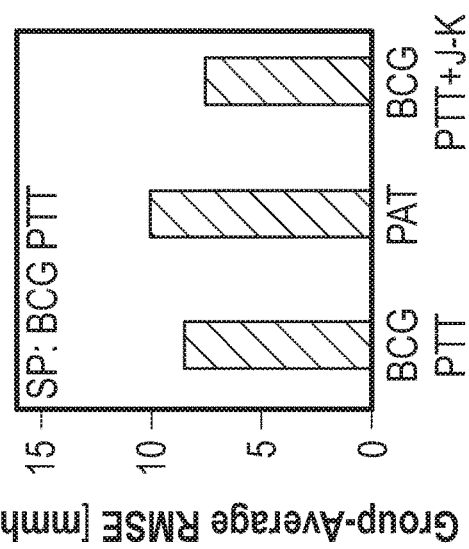
Figure 9C:
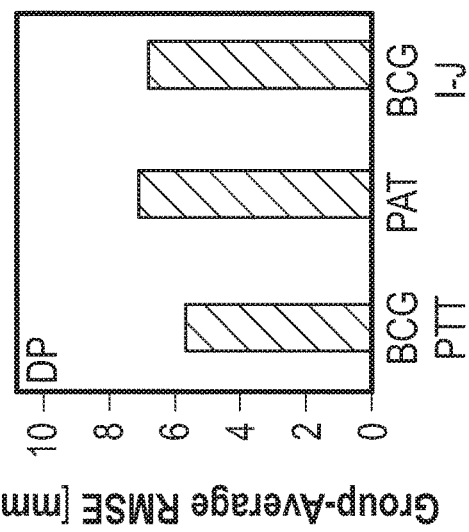

FIGS. 9A-9C show graphs of group average best-case root-mean-square error (RMSE) between reference DP and SP for corresponding calibrated DP surrogates, in accordance with various representative embodiments of the disclosure.

In regard to DP, as shown in FIG. 9A, the BCG I-J interval resulted in relatively good DP RMSEs that were comparable to the RMSEs associated with BCG-PTT and PAT. In regard to SP, as shown in FIG. 9B, multivariate linear regression of BCG-PTT and BCG J-K amplitude yielded smaller RMSEs than BCG PTT (by 12%; $p<0.002$) and PAT (by 25%; $p<0.015$). Further, as shown in FIG. 9C, multivariate linear regression of the BCG I-J interval and J-K amplitude to SP yielded relatively good SP RMSEs that were smaller than BCG I-J interval alone (by 28%; $p<0.01$) and PAT (by 16%). Finally, the BCG PTT-BCG J-K amplitude pair outperformed the BCG I-J interval-BCG J-K amplitude pair in monitoring SP, but the difference was not relatively significant.

FIGS. 8A-8C and 9A-9C thus demonstrate the efficacy of using BCG measurements to monitor both systolic and diastolic pressures, independently of each other. In accordance with embodiments of the disclosure, the BCG may enable independent and accurate monitoring of DP and SP. To date, PTT and PAT measured at the diastolic level (e.g., detected using the trough of the PPG waveform) have been used as ad-hoc surrogates of both DP and SP even though these levels are not well correlated. In contrast, the proposed approach can exploit mechanistically identified DP (I-J interval) and PP (J-K amplitude) surrogates to complement conventional PTT technique or even allow for independent and accurate tracking of DP and SP based on the BCG alone. In accordance with embodiments of the disclosure, methods and apparatus have been disclosed that enable BCG alone to be used for monitoring BP. Practically, this means that BP can be monitored in an ultra-convenient way. In contrast to the conventional PTT and PAT techniques that typically require the measurement of proximal and distal physiological signals (e.g., ECG and finger PPG for a PAT), the proposed approach may not require placement of any sensors on the body—for example, a force plate embedded on the floor of a checkout line in the grocery store, a weighing scale in a gym, a force plate in or under a chair, and the like may be used to monitor BP. Alternatively, in wearable settings, a single BCG sensor, such as an arm band or wrist band equipped with an accelerometer, may be used to implement cuff-less BP monitoring. In further embodiments, one or more accelerometers or other motion sensors may be coupled to a bed or chair and used to sense motion induced by cardiac forces in a subject. Other sensors, sensing techniques, or measurement techniques are also or instead possible.

Those skilled in the art will recognize that the present teachings have been described in terms of exemplary embodiments based upon use of a programmed processor. However, the teachings should not be so limited, since the present teachings could be implemented using hardware component equivalents such as special purpose hardware and/or dedicated processors which are equivalents to the teachings as described and claimed. Similarly, general purpose computers, microprocessor-based computers, microcontrollers, optical computers, analog computers, dedicated processors and/or dedicated hard wired logic may be used to construct alternative equivalent embodiments of the present teachings.

Moreover, those skilled in the art will appreciate that a program flow and associated data used to implement the embodiments described above can be implemented using various forms of storage such as Read Only Memory (ROM), Random Access Memory (RAM), Electrically Erasable Programmable Read Only Memory (EEPROM); non-volatile memory (NVM); mass storage such as a hard disc drive, floppy disc drive, optical disc drive; optical storage elements, magnetic storage elements, magneto-optical storage elements, flash memory, core memory and/or other equivalent storage technologies without departing from the present teachings. Such alternative storage devices should be considered equivalents.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another implementation, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another implementation, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared or other device or combination of devices. In another implementation, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the scope of this disclosure and are intended to form a part of the disclosure as defined by the following claims, which are to be interpreted in the broadest sense allowable by law.

The various representative embodiments, which have been described in detail herein, have been presented by way of example and not by way of limitation. It will be understood by those skilled in the art that various changes may be made in the form and details of the described embodiments resulting in equivalent embodiments that remain within the scope of the appended claims.

The various representative embodiments, which have been described in detail herein, have been presented by way of example and not by way of limitation. It will be understood by those skilled in the art that various changes may be made in the form and details of the described embodiments resulting in equivalent embodiments that remain within the scope of the appended claims.

What is claimed is:

1. A blood pressure monitor for sensing systolic and diastolic pressure levels of a subject, the blood pressure monitor comprising:
    a sensor configured to provide ballistocardiogram data in response to cardiac forces acting on the subject, where the ballistocardiogram data comprises a waveform having 'I', 'J' and 'K' peaks;
    a hardware processor configured to receive the ballistocardiogram data; and
    a non-transient computer readable medium accessible by the hardware processor and containing instructions that, when executed by the hardware processor, perform a method comprising:
        determining the diastolic pressure level from a time interval between the 'I' and 'J' peaks of the waveform;
        determining an amplitude difference between the 'J' and 'K' peaks of the waveform;
        determining a pulse pressure level from the amplitude difference between the 'J' and 'K' peaks of the waveform; and
        determining the systolic pressure level from the pulse pressure level and the diastolic pressure level;
        where the systolic and diastolic pressure levels are provided as outputs from the blood pressure monitor; and
        screening the subject for vascular diseases utilizing the systolic and diastolic pressure levels that are provided as outputs from the blood pressure monitor.

2. The blood pressure monitor of claim 1, where the sensor comprises a force plate.

3. The blood pressure monitor of claim 1, where the sensor comprises a bed.

4. The blood pressure monitor of claim 1, where the sensor comprises a chair.

5. The blood pressure monitor of claim 1, where the sensor comprises an acceleration, velocity, or displacement sensor.

6. The blood pressure monitor of claim 1, where the sensor comprises one or more body-mountable devices configured to sense whole-body motion in response to cardiac forces.

7. The blood pressure monitor of claim 6, where the one or more body-mountable devices configured to sense whole-body motion in response to cardiac forces comprises an accelerometer.

8. The blood pressure monitor of claim 1, where the non-transient computer readable medium is configured to store calibration data that is used in determining the pulse pressure level from the amplitude difference between the 'J' and 'K' peaks of the waveform.

9. The blood pressure monitor of claim 1, where the non-transient computer readable medium is configured to store calibration data that is used in determining the diastolic pressure level from the time interval between the 'I' and 'J' peaks of the waveform.

10. The blood pressure monitor of claim 1, further comprising a user interface configured to display the systolic and diastolic pressure levels.

\* \* \* \* \*